United States Patent
Han et al.

(10) Patent No.: US 10,683,386 B2
(45) Date of Patent: Jun. 16, 2020

(54) POWDER COATING LATENT CURING AGENT, AND EPOXY POWDER COATING COMPOSITION CONTAINING SAME

(71) Applicant: KCC CORPORATION, Seoul (KR)

(72) Inventors: Sang Hun Han, Yongin-si (KR); Seung Yeob Choi, Hwaseong-si (KR); Woo Ram Kim, Hwaseong-si (KR); Jee Hye Ann, Busan (KR); Byung Soo Moon, Imsil-gun (KR); Jun Tae Kang, Wanju-gun (KR)

(73) Assignee: KCC CORPORATION, Seoul (KR)

( * ) Notice: Subject to any disclaimer, the term of this patent is extended or adjusted under 35 U.S.C. 154(b) by 164 days.

(21) Appl. No.: 15/571,608

(22) PCT Filed: May 4, 2016

(86) PCT No.: PCT/KR2016/004690
§ 371 (c)(1),
(2) Date: Feb. 16, 2018

(87) PCT Pub. No.: WO2016/182259
PCT Pub. Date: Nov. 17, 2016

(65) Prior Publication Data
US 2018/0201720 A1    Jul. 19, 2018

(30) Foreign Application Priority Data

May 8, 2015 (KR) .................. 10-2015-0064704

(51) Int. Cl.
| | |
|---|---|
| *C08G 59/18* | (2006.01) |
| *C09D 5/03* | (2006.01) |
| *C09D 7/40* | (2018.01) |
| *C09D 7/63* | (2018.01) |
| *C07D 233/56* | (2006.01) |
| *C08G 59/50* | (2006.01) |
| *C08G 59/62* | (2006.01) |
| *C08L 63/00* | (2006.01) |
| *C09D 163/00* | (2006.01) |

(52) U.S. Cl.
CPC ......... *C08G 59/184* (2013.01); *C07D 233/56* (2013.01); *C08G 59/5073* (2013.01); *C08G 59/621* (2013.01); *C08L 63/00* (2013.01); *C09D 5/03* (2013.01); *C09D 5/033* (2013.01); *C09D 7/40* (2018.01); *C09D 7/63* (2018.01); *C09D 163/00* (2013.01)

(58) Field of Classification Search
None
See application file for complete search history.

(56) References Cited

U.S. PATENT DOCUMENTS

| | | | |
|---|---|---|---|
| 3,356,645 A * | 12/1967 | Warren | .............. C08G 59/5093 528/108 |
| 4,250,293 A | 2/1981 | Beitchman et al. | |
| 6,184,273 B1 | 2/2001 | December et al. | |
| 6,592,994 B2 | 7/2003 | McLeish et al. | |
| 2011/0028602 A1* | 2/2011 | Gan | ..................... C08G 59/686 523/429 |

FOREIGN PATENT DOCUMENTS

| | | |
|---|---|---|
| JP | 2008184598 | 8/2008 |
| JP | 2014047153 | 3/2014 |
| KR | 20070104621 | 10/2007 |
| KR | 20080105313 | 12/2008 |
| KR | 20110007172 | 1/2011 |
| KR | 20130108280 | 10/2013 |
| RU | 2086572 | 8/1997 |

OTHER PUBLICATIONS

International Search Report—PCT/KR2016/004690 dated Aug. 8, 2016.
Russian Office Action—Russian Application No. 2017135074 dated Jul. 6, 2018, citing KR 20080105313, KR 20110007172 and RU 2086572.
Russian Search Report—Russian Application No. 2017135074, dated Jul. 6, 2017, citing KR 20080105313, KR 20110007172 and RU 2086572.

* cited by examiner

*Primary Examiner* — Megan McCulley
(74) *Attorney, Agent, or Firm* — Cantor Colburn LLP

(57) ABSTRACT

Provided is a powder coating latent curing agent; and an epoxy powder coating composition having the same, and more specifically, to a powder coating latent curing agent, which is prepared by hot blending of a product of an addition reaction of imidazole, an amino alcohol and an epoxy resin with a phenolic curing agent resin, is capable of securing latency by inhibiting the reactivity of a phenolic curing agent, is capable of providing an improved coating film appearance and bending resistance when applied as a curing agent to a powder coating, and is capable of improving the workability of a coating preparation; and an epoxy powder coating composition having the same.

8 Claims, 3 Drawing Sheets

EXAMPLE          COMPARATIVE EXAMPLE

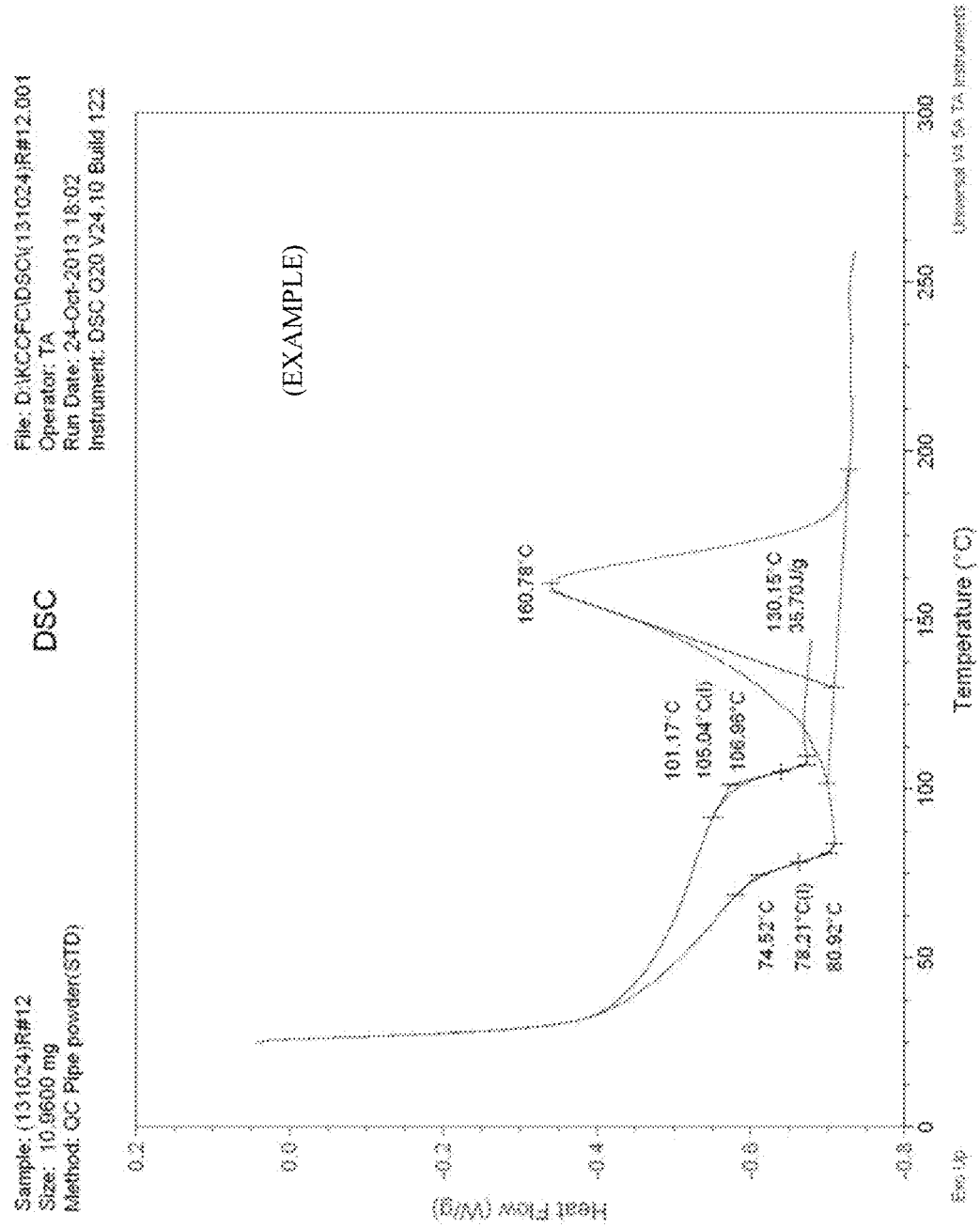

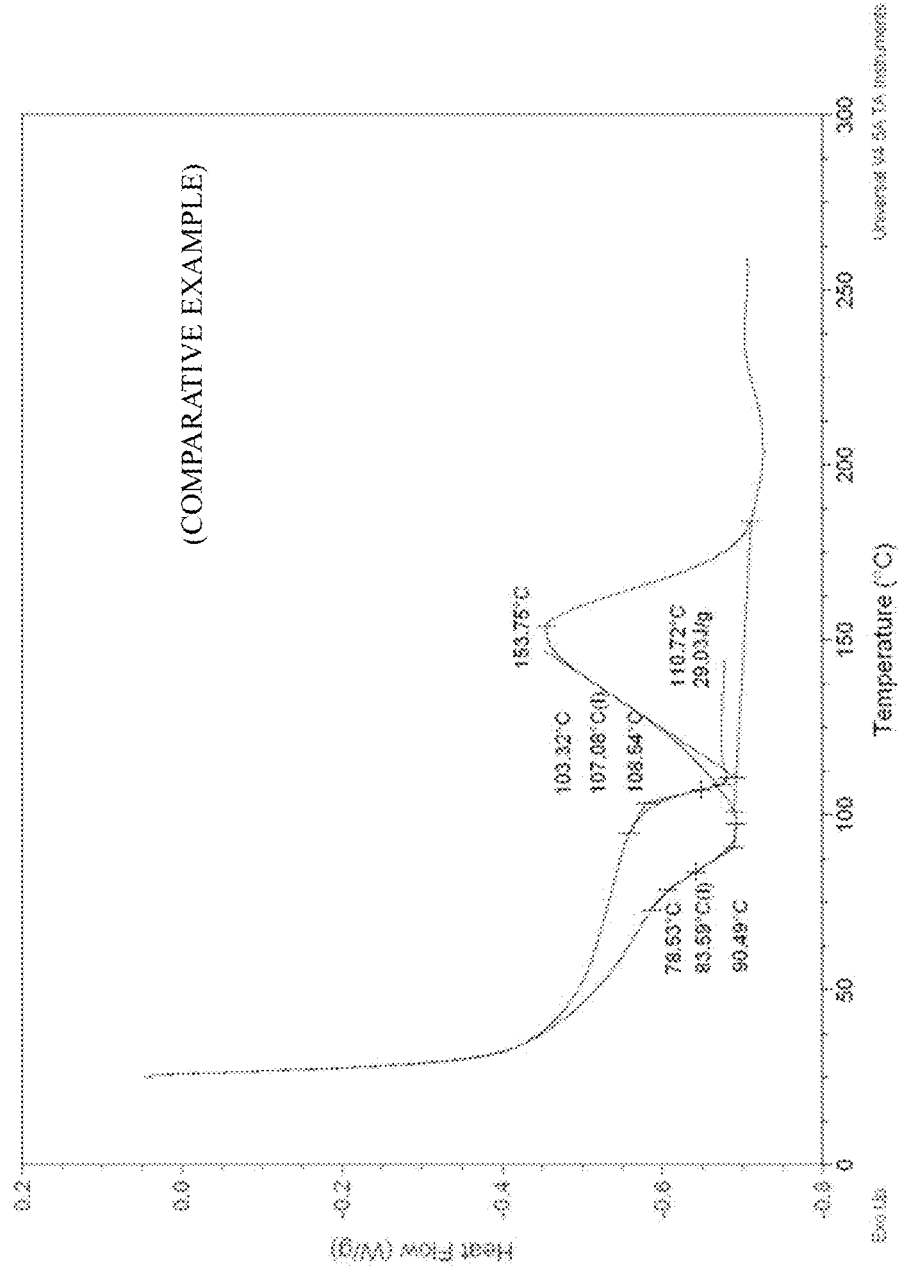

POWDER COATING LATENT CURING AGENT, AND EPOXY POWDER COATING COMPOSITION CONTAINING SAME

TECHNICAL FIELD

The present invention relates to a powder coating latent curing agent, and more specifically, to a powder coating latent curing agent, which is prepared by hot blending of a product of an addition reaction of imidazole, an amino alcohol and an epoxy resin with a phenolic curing agent resin. The powder coating latent curing agent may secure latency by inhibiting the reactivity of a phenolic curing agent, provide an improved coating film appearance and bending resistance when applied as a curing agent to a powder coating, and improve the coating workability. The present invention further relates to an epoxy powder coating composition having the powder coating latent curing agent.

BACKGROUND

U.S. Pat. No. 4,250,293 discloses a latent curing agent which is a salt of bisphenol-A (BPA) and an amine of dimethylaminopropylamines (DMAPAs), and an epoxy powder coating composition to which the same is applied.

Further, U.S. Pat. No. 6,184,273 discloses a coating composition having a latent curing agent produced by the reaction of alicyclic anhydrides (e.g., phthalic anhydride) and polyamine, and a carbonated epoxy resin.

In addition, U.S. Pat. No. 6,592,994 discloses a clear coating epoxy powder composition which uses a dicyandiamide (DICY) latent curing agent.

However, the latent curing agents disclosed in the aforementioned documents may show a poor coating workability due to insufficient latency. Although the dicyandiamide exhibits relatively excellent latency due to the high melting point, it may cause a deteriorated bending property when applied to a rebar powder coating.

DISCLOSURE OF THE INVENTION

Problems to be Solved

The present invention provides a powder coating latent curing agent, which is capable of securing latency by inhibiting the reactivity of a phenolic curing agent, is capable of providing an improved coating film appearance and bending resistance when applied as a curing agent to a powder coating, and is capable of improving the coating workability; and an epoxy powder coating composition having the same.

Means to Solve the Problems

The present invention provides a latent curing agent, which is prepared by hot blending of a product of an addition reaction (adduct) of imidazole, an amino alcohol and an epoxy resin with a phenolic curing agent resin.

The present invention further provides a powder coating composition including an epoxy resin as a base and the aforementioned latent curing agent.

Yet, the present invention provides a coated article (preferably a pipe or a rebar) including a coating film formed from the aforementioned powder coating composition.

Effects of the Invention

A latent curing agent according to the present invention and a powder coating composition having the same may provide an improved coating film appearance and bending resistance, and thus may be used particularly suitably for a fast curing-type coating of a material such as a pipe or a rebar.

BRIEF DESCRIPTION OF THE DRAWINGS

FIGS. 2A and 2B are a DSC analysis result for comparing the curing behaviors of the powder coatings in the Example (left side) and the Comparative Example (right side).

DETAILED DESCRIPTION TO EXECUTE THE INVENTION

Figure 1:
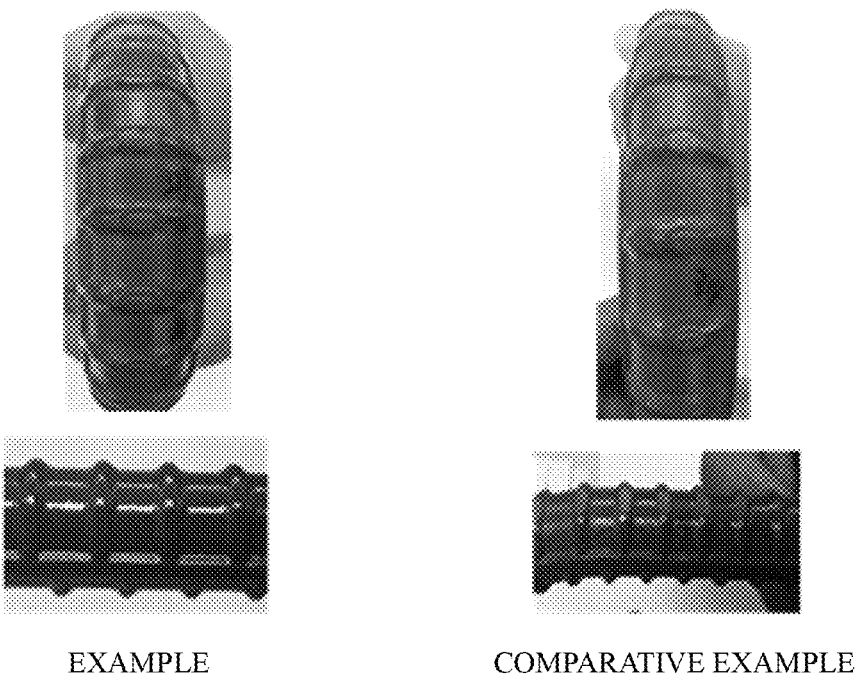
FIG. 1 is photographs of an appearance of a rebar coated with powder coatings in an Example (left side) and a Comparative Example (right side), respectively.

Hereinafter, the present invention will be described in detail.

A latent curing agent of the present invention is prepared by hot blending of a product of an addition reaction (adduct) of imidazole, an amino alcohol and an epoxy resin with a phenolic curing agent resin.

As the imidazole, an imidazole having one or more active hydrogens may be used, and for example, one or more imidazoles represented by the following Chemical Formula 1 may be used.

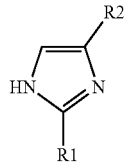

[Chemical Formula 1]

In Chemical Formula 1, R1 and R2 are the same as or different from each other, and represent hydrogen, an alkyl (for example, a $C_1$ to $C_6$ alkyl) or aryl (for example, a $C_6$ to $C_{18}$ aryl) group.

Specifically, as the imidazole, it is possible to use an imidazole selected from 2-methylimidazole, 2-phenylimidazole, 2-ethyl-4-methylimidazole and a mixture thereof. More preferably, 2-methylimidazole is used.

As the amino alcohol, it is possible to use an amine compound having one or more (for example, one to three) hydroxyalkyl groups, and specifically, it is possible to use an amine compound selected from monoalkanolamine (more specifically, mono($C_1$ to $C_6$)alkanolamine, for example, N-methylethanolamine), dialkanolamine (more specifically, di($C_1$ to $C_6$)alkanolamine, for example, diethanolamine), trialkanol alkaneamine (more specifically, tri($C_1$ to $C_6$)alkanol($C_1$ to $C_6$)alkane amine, for example, trimethylol aminomethane), and a mixture thereof. More specifically, diethanolamine is used.

As the epoxy resin, a bisphenol A type or bisphenol F type epoxy resin may be used, and the equivalent thereof may be specifically 100 to 1,500. More specifically, a liquid epoxy resin having an equivalent of 100 to 300, a solid epoxy resin having an equivalent of 400 to 1,500, or a mixture thereof may be used, and even more specifically, a liquid epoxy resin having an equivalent of 150 to 250 may be used.

When the product of an addition reaction of imidazole, an amino alcohol and an epoxy resin is prepared, the amount of these components used is not particularly limited, but the imidazole may be used in an amount of 10 to 30 parts by weight (more specifically, 15 to 25 parts by weight), the amino alcohol may be used in an amount of 5 to 20 parts by weight (more specifically, 10 to 15 parts by weight), and the epoxy resin may be used in an amount of 50 to 80 parts by weight (more specifically, 60 to 75 parts by weight), based on 100 parts by weight, which is the total sum of the imidazole, the amino alcohol, and the epoxy resin.

Further, for the equivalent ratio of imidazole and amino alcohol used, the equivalent of imidazole may be equal to or greater than the equivalent of amino alcohol, and for example, the equivalent of imidazole:the equivalent of amino alcohol may be 3:1 to 1:3, but the equivalent ratio is not limited thereto. When the equivalent of imidazole is higher than the range, the curing rate becomes fast, so that there may be a problem in that the latency deteriorates. Further, the amount of liquid amino alcohol is relatively small, so that an unnecessary solvent needs to be further used in order to solve the solid imidazole during an addition reaction with an epoxy resin. In contrast, when the equivalent of imidazole is lower than the range, there may be a problem in that the curing rate drops.

The addition reaction of the imidazole, the amino alcohol, and the epoxy resin is an exothermic reaction, and thus may be carried out in an appropriate solvent. An available solvent may be selected from a polar solvent such as alcohol, a non-polar solvent such as toluene and xylene, and a mixture thereof. In addition, the addition reaction of the imidazole, the amino alcohol and the epoxy resin may be carried out at an elevated temperature (for example, elevated within a temperature range of 90° C. to 120° C.).

As the phenolic curing agent resin, it is possible to use a phenolic curing agent resin which is prepared by reacting a phenol compound with an epoxy resin, and the molecular weight thereof may be, for example, 200 to 1,000, more specifically, 400 to 800.

When the phenolic curing agent resin is prepared, as a phenol compound, a phenol compound selected from bisphenol A (BPA), bisphenol F (BPF), and a mixture thereof may be used, and as an epoxy resin, those previously described may be used.

When the phenol curing agent resin is prepared, the amount of phenol compound and epoxy resin used is not particularly limited, and for example, the phenol compound and the epoxy resin may be used in an amount of 40 to 80 parts by weight (more specifically, 50 to 70 parts by weight) and 20 to 60 parts by weight (more specifically, 30 to 50 parts by weight), respectively, based on 100 parts by weight, which is the total sum of the phenol compound and the epoxy resin.

The reaction of the phenol compound and the epoxy resin may be carried out in the presence of an appropriate catalyst. An available catalyst may be selected from a phosphorus-based catalyst (for example, ethyltriphenylphosphonium bromide, ethyltriphenylphosphonium iodide, and the like), an amine-based catalyst (for example, 2-ethyl-4-methylimidazole, and the like), and a mixture thereof. Further, the reaction of the phenol compound and the epoxy resin may be carried out at an elevated temperature (for example 120° C. to 200° C.).

The latent curing agent of the present invention is prepared by hot blending of the product of the addition reaction of the imidazole, the amino alcohol and the epoxy resin with the phenolic curing agent resin. The amount of phenolic curing agent resin blended may be, for example, 100 to 150 parts by weight, more specifically, 110 to 140 parts by weight, based on 100 parts by weight of the product of the addition reaction of the imidazole, the amino alcohol and the epoxy resin, but is not limited thereto.

The hot blending of the product of the addition reaction of the imidazole, the amino alcohol and the epoxy resin with the phenolic curing agent resin may be carried out, for example, at 80° C. to 200° C. During the hot blending, or after the hot blending, the residual solvent in the mixture is removed, and as a result, it is possible to obtain a latent curing agent in the form of a powder having a solid content of 99% or more.

The present invention further provides a powder coating composition including an epoxy resin as a base and the aforementioned latent curing agent of the present invention.

As the base epoxy resin, which is included in the powder coating composition of the present invention, an epoxy resin having an equivalent of, for example, 800 to 1,200 (more specifically, 900 to 1,000) may be used, and specifically, it is possible to use an epoxy resin selected from a bisphenol A type epoxy resin, a bisphenol F type epoxy resin and a mixture thereof.

The amount of the base epoxy resin, which is included in the powder coating composition of the present invention, may be, for example, 40 to 80 parts by weight, more specifically, 50 to 70 parts by weight based on the total 100 parts by weight of the coating composition. Further, the amount of latent curing agent included in the powder coating composition of the present invention may be, for example, 5 to 20 parts by weight, more specifically, 8 to 15 parts by weight based on the total 100 parts by weight of the coating composition.

The powder coating composition of the present invention is characterized by including the aforementioned latent curing agent as a curing agent, but this does not mean that the use of another curing agent is excluded. That is, the powder coating composition of the present invention may additionally include an existing powder coating curing agent (for example, a phenolic curing agent), if necessary, within a range capable of achieving the object of the present invention, in addition to the latent curing agent described above.

Further, the powder coating composition of the present invention may further include one or more additives (for example, a pigment, a flow improver, a filler, and the like) typically used for the powder coating in an amount typically used for the powder coating, in addition to the aforementioned components.

A method for preparing the powder coating composition of the present invention is not particularly limited, and the powder coating composition may be prepared by using a typical method and equipment for preparing a powder coating as it is, or appropriately modifying the typical method and equipment.

Hereinafter, the present invention will be described in detail through Examples. However, the following Examples are only for exemplifying the present invention, and the scope of the present invention is not limited to the following Examples.

Examples

Preparation Example of Latent Curing Agent

1) Preparation of Product of Addition Reaction of Imidazole, Amino Alcohol and Liquid Epoxy Resin 110 g of 2-methylimidazole, 80 g of diethanolamine, and 30 g of butanol were subsequently introduced into a 4-necked flask equipped with a thermometer and a stirrer, and the flask was slowly warmed to 100° C. while blowing a nitrogen gas into the flask. 370 g of a liquid bisphenol A epoxy resin having an equivalent of 190 was slowly introduced thereinto while controlling the generation of heat, and then the flask was maintained at the same temperature for 2 hours or more. Thereafter, the reaction mixture was cooled and diluted with a xylene solvent to obtain an intermediate resin which is a product of the addition reaction of imidazole, an amino alcohol and a liquid epoxy resin (solid content 65%).

2) Preparation of Phenolic Curing Agent 400 g of bisphenol A and 250 g of a liquid bisphenol A epoxy resin were subsequently introduced into a 4-necked flask equipped with a thermometer and a stirrer, and the flask was slowly warmed to 140° C. while blowing a nitrogen gas into the flask. At the time when the bisphenol A was completely dissolved, 0.1 g of ethyltriphenylphosphonium iodide was introduced thereinto, and then the flask was warmed to 180° C. and maintained for 2 hours or more. After the flask was maintained, the flask was cooled to room temperature to prepare a phenolic curing agent resin in the form of a powder.

3) Preparation of Latent Curing Agent 500 g of the intermediate resin prepared in Process 1) was introduced into the phenolic curing agent resin prepared in Process 2), the solvent was removed while performing hot blending to prepare a latent curing agent resin in the form of a powder having a solid content of 99% or more.

Preparation Example of Powder Coating Composition

The components having the content shown in the following Table 1 were used to prepare the powder coating compositions, respectively, in the Example and the Comparative Example. As the curing agent, the latent curing agent prepared in the Preparation Example was used in the Example, and an existing phenolic curing agent was used in the Comparative Example.

As a first step process, raw materials such as a base, a curing agent, a catalyst, a pigment, and an additive were uniformly mixed, and then the resulting mixture was dry premixed at 2,000 to 5,000 rpm for about 100 to 600 seconds by using a Henschel mixer to carry out a pre-mixing process of dry mixing the mixture so as to maintain uniform physical properties during the melt mixing.

As a second step process, the raw materials, which were subjected to the first step process and pre-dispersed, were melted, mixed, and dispersed at a temperature of 90° C. to 120° C. by using a disperser (PLK 46, Buss AG Basel). The melted and mixed raw materials were allowed to pass through a cooling roll and a cooling belt to prepare chips having a size of 50 mm to 100 mm and a thickness of 1 mm to 5 mm.

As a third step process, the chips, which were subjected to the second step process, melted, mixed, and dispersed, were mechanically ground (average particle size: 40 μm to 60 μm) by using a grinder (hammer mill).

TABLE 1

(Content unit: Part by weight)

| Component | Example | Comparative Example |
|---|---|---|
| Base | 60 | 60 |
| Curing agent (1) | — | 11.3 |
| Curing agent (2) | 12.3 | — |
| Catalyst | — | 1 |
| Pigment (1) | 3 | 3 |

TABLE 1-continued (Content unit: Part by weight)

| Component | Example | Comparative Example |
|---|---|---|
| Pigment (2) | 5 | 5 |
| Additive | 0.3 | 0.3 |
| Filler | 19.4 | 19.4 |
| Total | 100 | 100 |

Base: Bisphenol A Type Epoxy Resin (Equivalent: 900 to 1,000)
Curing agent (1): Phenolic curing agent in Preparation Example 2)
Curing agent (2): Latent curing agent in Preparation Example 3)
Catalyst: 2-methylimidazole (Shikoku Chemicals Corp.)
Pigment (1): Colored pigment/Bayferrox 130M (Bayer)
Pigment (2): Colored pigment/CR-80 (Ishihara Co., Ltd.)
Additive: Flow improver (PLP-100, KS Chemical)
Filler: Omyacarb 5 (Omya Korea)

Test Examples

A rebar rod having a diameter of 19 mm, which was subjected to blast treatment in advance, was coated with each of the powder coating composition in the Example and the Comparative Example to a thickness of 200 μm to 500 μm by an electrostatic spray coater, while being pre-heated to 180° C. to 250° C. Thereafter, the coated rebar rod was left to stand at room temperature for about 1 minute, and immediately immersed in cold water to form a final coating film. For the coated test specimen and powder coating, the following items were measured and evaluated, and the results are shown in Table 2.

Bending Property

In accordance with the ASTM A776, it was measured whether a coating film was broken when a test specimen obtained from the rebar rod subjected to blast treatment was bent in a bending property tester using a 114 mm mandrel.

Curability (1) ΔTg: A powder coating is uniformly coated to a thickness of 300 μm to 400 μm onto a hot plate at a temperature of 232° C. The coating film is collected 30 seconds after the coated powder coating forms the coating film, and is immersed in cold water. For the collected coating film, ΔTg is obtained using a differential scanning calorimeter (DSC). The smaller ΔTg is, the better the coating film is.

(2) Gel Time: About 1 g of the powder coating is applied onto a hot plate at a temperature of 200° C., and then the instant when the viscosity is suddenly increased is measured. The range obtained by repeating the measurement several times is shown in Table 2.

Negative Electrode Peeling Property

A test rod is manufactured by perforating the coated rebar rod with holes having a diameter of 3 mm. A cylinder having a diameter of 3.5 inches is filled with a 3% NaCl solution, and a platinum wire and the test rod are dipped into the solution. Thereafter, a voltage of 1.5 V is applied to the platinum wire and the test rod for 7 days. After 7 days, the rod is taken out, 8 parts around the 3-mm holes perforated in the initial stage are radially scratched with a knife until the rods are exposed, the knife is pushed between the coating film and the rod at the peeling site of the coating film to measure the adhesive property by the principle of the lever, and then the average of the lengths thereof is obtained. The shorter the average length is, the better the negative electrode peeling property is. The range obtained by repeating the measurement several times is shown in Table 2.

Appearance (Observation by Naked Eye)

The appearance of the coated rebar was observed by the naked eye and evaluated. Further, FIG. 1 illustrates photographs of an appearance of a rebar coated with the powder coatings in the Example (left side) and the Comparative Example (right side), respectively.

Comparison of Curing Behaviors

In order to compare the curing behaviors, each of the powder coatings in the Example and the Comparative Example was subjected to the DSC analysis, and the results are shown in FIGS. 2A and 2B.

Referring to FIGS. 2A and 2B, it can be confirmed that the curing onset temperature in the Example is 130.15° C., and the curing onset temperature in the Comparative Example is 110.72° C. That is, the curing onset temperature of the powder coating to which the latent curing agent is applied is shifted to a higher temperature, and the temperature shift delays the curing which may instantaneously occur when the pre-heated (180° C. to 250° C.) object is coated with the powder coating. For this reason, the wetting property of the coating toward the object may be improved (that is, there is a temporal leeway which may have wettability), which leads to excellent adhesive property, bending property, and appearance of the coating.

Further, referring to Table 2 and FIGS. 2A and 2B, an amount of heat generated in the Examples is higher than that in the Comparative Example, and ΔTg in the Example approaches 0. ΔTg approaching 0 means that the curing is completely performed, and the higher ΔTg value means that the curing is less performed. That is, it can be confirmed that in the case of the Example, the curing is completely performed, and accordingly, physical properties are improved as compared to the Comparative Example.

TABLE 2

| Item | Example | Comparative Example |
|---|---|---|
| Bending property | No breakage of coating film | Occurrence of breakage of coating film |
| ΔTg (° C.) | 0.40 | 1.89 |
| Gel Time (sec) | 11.5 to 12.0 | 9.5 to 10.0 |
| Negative electrode peeling property (mm) | 3.1 to 4.0 | 3.8 to 5.0 |
| Appearance | Excellent | Good |
| Workability | Facilitated during mass production | Not well coated |
| Curing onset temperature (° C.) | 130.15 | 110.72 |

TABLE 2-continued

| Item | Example | Comparative Example |
|---|---|---|
| Exothermic peak curve | Steep | Gradual |
| Amount of heat generated (J/g) | 35.7 | 29.0 |

The invention claimed is:

1. A latent curing agent which is prepared by hot blending of a product of an addition reaction of imidazole, an amino alcohol and an epoxy resin with a phenolic curing agent resin, wherein an equivalent of imidazole: an equivalent of amino alcohol is 3:1 to 1:3, and wherein the hot blending is carried out at 80° C. to 200° C.

2. The latent curing agent of claim 1, wherein the imidazole has one or more active hydrogens, and is one or more represented by the following chemical formula:

[Chemical Formula 1]

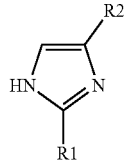

in Chemical Formula 1, R1 and R2 are the same as or different from each other, and represent hydrogen, an alkyl or aryl group.

3. A powder coating composition comprising:
an epoxy resin as base; and
the latent curing agent according to claim 2.

4. The latent curing agent of claim 2, wherein the imidazole is selected from the group consisting of 2-methylimidazole, 2-phenylimidazole, 2-ethyl-4-methylimidazole, and a mixture thereof.

5. A powder coating composition comprising:
an epoxy resin as base; and
the latent curing agent according to claim 4.

6. The latent curing agent of claim 1, wherein the amino alcohol is selected from the group consisting of mono alkanolamine, dialkanolamine, trialkanol alkaneamine, and a mixture thereof.

7. A powder coating composition comprising:
an epoxy resin as base; and
the latent curing agent according to claim 6.

8. A powder coating composition comprising:
an epoxy resin as base; and
the latent curing agent according to claim 1.

* * * * *